(12) United States Patent
Saxena et al.

(10) Patent No.: US 8,703,881 B2
(45) Date of Patent: *Apr. 22, 2014

(54) CURABLE COMPOSITIONS OF IONIC SILICONES

(71) Applicant: Momentive Performance Materials Inc., Albany, NY (US)

(72) Inventors: Anubhav Saxena, Bangalore (IN); Srividhya Marimuthu, Bangalore (IN); Pranav Ramchandra Joshi, Bangalore (IN); Alok Sarkar, Malda (IN)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/722,165

(22) Filed: Dec. 20, 2012

(65) Prior Publication Data

US 2013/0171265 A1  Jul. 4, 2013

Related U.S. Application Data

(60) Provisional application No. 61/582,921, filed on Jan. 4, 2012.

(51) Int. Cl.
   *C08G 77/22* (2006.01)
(52) U.S. Cl.
   USPC ............ 525/477; 528/15; 528/26; 528/30; 528/31; 528/38; 528/41; 528/25
(58) Field of Classification Search
   None
   See application file for complete search history.

(56) References Cited

U.S. PATENT DOCUMENTS

| | | | |
|---|---|---|---|
| 2,968,643 A | 1/1961 | Bailey | |
| 4,495,340 A | 1/1985 | Blizzard et al. | |
| 4,523,002 A | 6/1985 | Campbell et al. | |
| 4,525,567 A | 6/1985 | Campbell et al. | |
| 5,532,399 A | 7/1996 | Hager et al. | |
| 2008/0293878 A1* | 11/2008 | Funk et al. | 524/588 |
| 2010/0027267 A1 | 2/2010 | Hamilton | |
| 2013/0172193 A1* | 7/2013 | Saxena et al. | 504/360 |
| 2013/0172419 A1* | 7/2013 | Saxena et al. | 514/570 |
| 2013/0172427 A1* | 7/2013 | Saxena et al. | 514/772.1 |

FOREIGN PATENT DOCUMENTS

| | | |
|---|---|---|
| DE | 10 2005 057 460 A1 | 6/2007 |
| EP | 0581296 A2 | 7/1993 |
| JP | 6247827 A | 9/1994 |
| JP | 6247835 A | 9/1994 |
| WO | 2006065467 A2 | 6/2006 |

OTHER PUBLICATIONS

International Search Report and Written Opinion dated on May 29, 2013.

* cited by examiner

*Primary Examiner* — Marc Zimmer
(74) *Attorney, Agent, or Firm* — Dominick G. Vicari

(57) ABSTRACT

A curable composition of ionic silicones includes a silicone having the formula $M^1_a M^2_b M^3_c D^1_d D^2_e D^3_f T^1_g T^2_h T^3_i Q_j$ having ionic groups and crosslinking functional groups. The composition can further include polyorganosiloxane having the average compositional formula $R^{26}_n R^{27}_o (OH)_p SiO_{(4-n-o-p)/2}$, organohydrogenoligosiloxane or organohydrogenpolysiloxane that has the average compositional formula $H_q R^{28}_r SiO_{(4-q-r)/2}$ a transition metal catalyst and other components such as UV stabilizer, cure accelerator, pigment, dye, antimicrobial agent, biocide, surfactant, functional or non-functional filler, conductive filler, finely divided surface treated/untreated metal oxides, clay, plasticizers, tackifiers, mold release agents, adhesion promoters, compatibilizers, pharmaceutical excipients, surfactants or antistatic agents.

29 Claims, 5 Drawing Sheets

CURABLE COMPOSITIONS OF IONIC SILICONES

CROSS-REFERENCE TO RELATED APPLICATIONS

The present application claims priority to U.S. provisional application No. 61/582,921 filed Jan. 4, 2012 which is herein incorporated by reference.

BACKGROUND

This invention relates to curable compositions containing silicone ionomers which are the polyorganosiloxanes containing ionic groups and at least one functional group that can undergo addition or dehydrogenative condensation cure. This makes them very useful in many different applications in elastomer, RTV, and gels including those for personal care, health care applications such as wound dressings, dressings for scar reduction, transdermal drug delivery patches, medical tubing, clinical surfaces, surgical devices, pacemaker leads, household applications, apparel, sporting goods such as diving masks, paints, coatings, fuel cell, electronic and electro-optic applications, agriculture, membranes, injection moldable and compression moldable rubbers and plastics, and various silicone based rubbers.

U.S. Pat. No. 2,968,643 describes the sulfo-arylalkyl siloxanes, their salts and a process for the preparation.

JP patents 6,247,827 and JP 6,247,835 disclose a process for preparing sulfonate functionalized silicones and their use in personal care application.

U.S. Pat. Nos. 4,525,567 and 4,523,002 describe polyorganosiloxane functionalized with zwitterionic sulfonate groups and a method of preparation.

WO 2006065467 discloses sulfonate-based ionic silicones and methods for making them via the reaction of an aminopolyorganosiloxanes with sulfonate containing acid anhydride.

EP581296 A2 discloses polyether functionalized sulfonated-polyorganosiloxanes and method of preparation via hydrosilylation of a hydride-containing polyorganosiloxane with allyl-polyether and p-chloromethylstyrene followed by substitution of the chloro-group in presence of aqueous lithium sulfite solution.

However, the above mentioned methods do not disclose the polyorganosiloxane ionomers bearing reactive functional groups such as silicon-hydride, or vinyl, as part of the polymer chain.

The present invention comprises ionic silicones that are made curable on account of the incorporation of reactive functional groups such as -silicon-hydride, -vinyl in the ionic silicone chain. These ionic silicones can be cured to yield various elastomer compositions such as gels and rubbers comprising ionic groups. The presence of ionic groups imparts differentiating properties to the elastomer compositions thereby making them useful in applications such as healthcare, personal care, automotive, coatings, electrical and electronics, household applications, agriculture, oil and gas, textiles and sporting goods.

SUMMARY

A curable composition containing an ionic silicone is provided herein. The ionic silicone has the following formula (I):

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$.

$R^1$, $R^2$, $R^5$, $R^6$, $R^8$, $R^9$, $R^{11}$, $R^{13}$, and $R^{15}$ are aliphatic, aromatic or fluoro monovalent hydrocarbons having from 1 to 60 carbon atoms, $R^3$, $R^{10}$, $R^{16}$ can be independently chosen from glycolide {—C(O)CH$_2$O—}, lactide {—C(O)CH(CH$_3$)O—}, butyrolactide {—C(O)CH$_2$CH$_2$CH$_2$O—} and caprolactide {—C(O)CH$_2$CH$_2$CH$_2$CH$_2$CH$_2$O—} radicals or hydrocarbon radical defined by $R^1$.

$R^4$, $R^{12}$, $R^{17}$ are monovalent radical-bearing ion-pairs having the formula (II) or zwitterions having formula (III), wherein formula (II) is as follows, $$A\text{-}I^{x-}M_n^{y+} \quad (II);$$

where A is a spacing group having at least one spacing atoms selected from a divalent hydrocarbon or hydrocarbonoxy group, I is an ionic group selected from sulfonate —SO$_3^{31}$, sulfate —OSO$_3^-$, carboxylate —COO$^-$, phosphonate —PO$_3^{2-}$ and phosphate —OPO$_3^{2-}$ groups, M is hydrogen or a cation independently selected from alkali metals, alkaline earth metals, rare earth metals, transition metals, metals, metal complexes, quaternary ammonium and phosphonium groups, hydrocarbon cations, alkyl cations, organic cations, and cationic polymers. The zwitterions have the formula (III), $$R'\text{—}NR''_2^+\text{—}R'''\text{—}I^- \quad (III)$$

where R' is a divalent hydrocarbon radical containing from 1 to about 60 carbon atoms, R'' is monovalent hydrocarbon radical containing from 1 to about 60 carbon atoms, R''' is divalent hydrocarbon radical containing from 2 to about 20 carbon atoms, specifically from 2 to about 8 carbon atoms and more specifically from 2 to about 4 carbon atoms; and, I is an ionic group selected from sulfonate —SO$_3^-$, sulfate —OSO$_3^-$, carboxylate —COO$^-$, phosphonate —PO$_3^{2-}$ and phosphate —OPO$_3^{2-}$ groups, where $R^7$, $R^{14}$ and $R^{18}$ are independently selected from hydrogen, or unsaturated monovalent radicals or epoxy group containing radicals, where subscripts n and y are independently selected from 1 to 6 and x is a product of n and y, and the subscript a, b, c, d, e, f, g, h, i, j are zero or positive subject to the following limitations: the sum a+b+c+d+e+f+g+h+i+j is greater than or equal to 2 or less than or equal to 6000, the sum b+e+h is greater than zero and the sum c+f+i is greater than zero.

BRIEF DESCRIPTION OF THE DRAWINGS

Various embodiments are described below with reference to the drawings wherein.

DETAILED DESCRIPTION OR PREFERRED EMBODIMENT(S)

Figure 1:
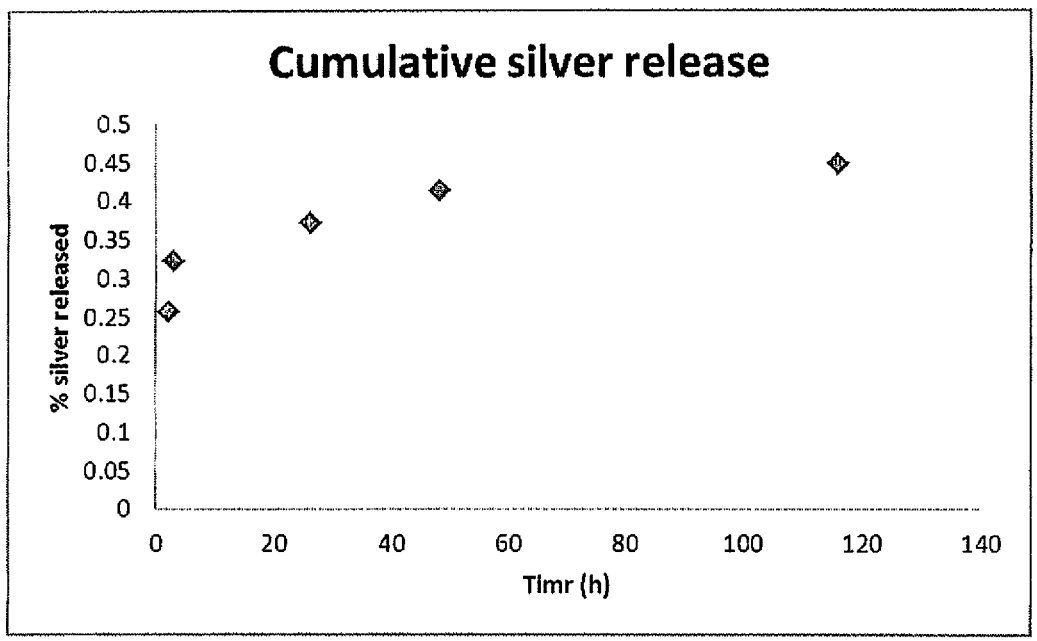
FIG. 1 is a graph showing the release of silver with time from an addition cured silicone elastomer containing an ionic silicone with sulfonate groups.

As used in the specification and including the appended claims, the singular forms "a," "an," and "the" include the plural, and reference to a particular numerical value includes at least that particular value, unless the context clearly dictates otherwise.

Ranges expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "hydrocarbon" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

It will be understood herein that all measures of viscosity are obtained at 25 degrees Celsius unless noted otherwise.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

In the present invention, there is provided an addition curable ionic silicone composition which comprises components (A), (B), (C), (D), (E), and (F) as follows.

Component (A):

Component (A) comprises an ionic silicone of the following formula (I):

$$M^1_a M^2_b M^3_c D^1_d D^2_e D^3_f T^1_g T^2_h T^3_i Q_j. \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ wherein $R^1$, $R^2$, $R^5$, $R^6$, $R^8$, $R^9$, $R^{11}$, $R^{13}$, and $R^{15}$ are aliphatic, aromatic or fluoro monovalent hydrocarbon having from 1 to 60 carbon atoms. Example of useful hydrocarbon groups includes methyl, ethyl, n-propyl, iso-propyl, n-butyl, isobutyl, tert-butyl, n-pentyl, iso-pentyl, neopentyl and tert-pentyl; hexyl, such as the n-hexyl group; heptyl, such as the n-heptyl group; octyl, such as the n-octyl and isooctyl groups and the 2,2,4-trimethylpentyl group; nonyl, such as the n-nonyl group; decyl, such as the n-decyl group; cycloalkyl radicals, such as cyclopentyl, cyclohexyl and cycloheptyl radicals and methylcyclohexyl radicals. Examples of aryl groups include phenyl, naphthyl; o-, m- and p-tolyl, xylyl, ethylphenyl, and benzyl, wherein $R^3$, $R^{10}$, $R^{16}$ are independently selected from $-CH_2CH(R')(C_nH_2n)-O-(C_2H_4O)_o-(C_3H_6O)_p-(C_4H_8O)_q-R'$, wherein subscript n is zero or positive and has a value in the range of 0 to 6, subscripts o, p and q are zero or positive and independently selected from a value in the range of 0 to 100, subject to the limitation of o+p+q greater than or equal to 1. R' can be hydrogen or an aliphatic, aromatic or fluoro hydrocarbon having from 1 to 60 carbon atoms, or R' can be independently chosen from glycolide $\{-C(O)CH_2O-\}$, lactide $\{-C(O)CH(CH_3)O-\}$, butyrolactide $\{-C(O)CH_2CH_2CH_2O-\}$ and caprolactide $\{-C(O)CH_2CH_2CH_2CH_2CH_2O-\}$ radicals or hydrocarbon radical defined by $R^1$.

$R^4$, $R^{12}$, and $R^{17}$ are monovalent radical-bearing ion-pairs having the formula (II)

$$A-I^{x-}M_n^{y+} \qquad (II);$$

where A is a spacing group having at least one spacing atom selected from a divalent hydrocarbon or hydrocarbonoxy group, where I is ionic groups such as sulfonate $-SO_3^-$, sulfate $-OSO_3^-$, carboxylate $-COO^-$, phosphonate $-PO_3^{2-}$, or phosphate $-OPO_3^{2-}$ groups, more specifically sulfonate $-SO^{3-}$, where M is hydrogen or a cation independently selected from alkali metals, alkaline earth metals, rare earth metals, transition metals, metal complexes, quaternary ammonium and phosphonium groups, hydrocarbon cations, alkyl cations, organic cations, and cationic polymers.

Alternatively, $R^4$, $R^{12}$, and $R^{17}$ can be zwitterions having the formula (III):

$$R'-NR''_2^+-R'''-I \qquad (III)$$

where

R' is a divalent hydrocarbon radical containing from 1 to about 60 carbon atoms, specifically from 1 to about 20 carbon atoms, and more specifically from 1 to about 8 carbon atoms, R'' is monovalent hydrocarbon radical containing from 1 to about 60 carbon atoms, specifically from 1 to about 20 carbon atoms and more specifically from 1 to about 8 carbon atoms, and where R''' is divalent hydrocarbon radical containing from 2 to about 20 carbon atoms, specifically from 2 to about 8 carbon atoms and more specifically from 2 to about 4 carbon atoms; and, I is an ionic group such as sulfonate $-SO_3^-$, sulfate $-OSO_3^-$, carboxylate $-COO^-$, phosphonate $-PO_3^{2-}$, or phosphate $-OPO_3^{2-}$ groups where $R^7$, $R^{18}$ are independently selected from, hydrogen, or unsaturated monovalent radicals or epoxy group containing radicals where $R^{14}$ is independently selected from hydrogen, unsaturated monovalent radicals or epoxy group containing radicals or hydrogen when the ionic group is not a zwitter ion represented by the formula (III) above where subscript n and superscript y are independently from 1 to 6 and x is the product of n times y, where the subscript a, b, c, d, e, f, g, h, i, j are zero or positive subject to the following limitations: to the sum a+b+c+d+e+f+g+h+i+j is greater than or equal to 2, and less than or equal to 6000, specifically the sum a+b+c+d+e+f+g+h+i+j is greater than or equal to 2 and less than or equal to 4000, more specifically the sum a+b+c+d+e+f+g+h+i+j is greater than or equal to 2 and less than or equal to 2000, the sum b+e+h greater than 0 and the sum c+f+i greater than 0.

In one other embodiment herein the divalent hydrocarbon group of A in formula (II) is an arylene group selected from the group consisting of $-(CH_2)_lC_6H_4(CH_2)_k-$, $-CH_2CH(CH_3)(CH_2)_kC_6H_4-$, $-CH_2CH(R^1)(CH_2)_lC_6H_3R^{19}-$ and $-CH_2CH(R^1)(CH_2)_lC_6H_2R^1R^{19}-$ where $R^1$ is as defined, $R^{19}$ is a monovalent radical specifically from about 1 to about 20 carbon atoms, more specifically from about 1 to about 8 carbon atoms, sulfur atom(s), nitrogen atom(s), oxygen atom(s) or a radical containing combinations of the above atoms, where l has a value of 0 to 20, specifically from 1 to about 10 and k has a value of 0 to 20, specifically from 0 to about 10.

In another embodiment, the divalent hydrocarbon group of A in formula (II) is an alkylene group of the formula $-(CHR^{20})_m-$ where m has a value of 1 to 20, specifically, from 1 to about 10 and $R^{20}$ is hydrogen or $R^1$.

In another embodiment the divalent hydrocarbonoxy group of A in formula (II) is selected from $(CHR^{20})_m-(OCH(R^{20})(CH_2)_p-O-(CH_2)_l-$ where l has a value of from 0 to 20, specifically from 1 to about 10, m has a value of 0 to 50 and p has the value from 1 to 50.

In one other embodiment, in formula (II) M can be a cation independently selected from Li, Na, K, Cs, Mg, Ca, Ba, Zn, Cu, Fe, Ni, Ga, Al, Mn, Cr, Ag, Au, Pt, Pd, Pb, Sb, Ru, Sn, Rh Ce, Eu, Co, Gd and La. One skilled in the art can understand that the cations can exist in multivalent forms e.g., $Mn^{+2}$ and $Mn^{+3}$.

$R^7$, $R^{14}$, and $R^{18}$ are curable functional groups independently selected from monovalent radical containing reactive groups of the following general formulae:

(IV)

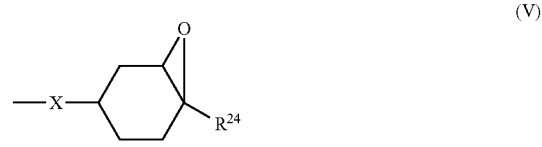

(V)

(VI)

wherein $R^{21}$ to $R^{25}$ are independently selected from hydrogen, aliphatic/aromatic monovalent hydrocarbon having from 1 to 60 carbon atoms, X is a divalent hydrocarbon linkage consisting of 1 to 60 carbon atoms and 0 to heteroatoms such as oxygen, nitrogen and sulfur.

Component (B):

Component (B) comprises 0-99 parts by weight of reinforcing filler or non-reinforcing filler selected from silica, fumed silica, nano silica, functionalized or unfuctionalized silicone resins, natural and synthetic fibers, polysaccharides, cork, graphite and carbon black, carbon nanotubes, graphene, clay, boron nitride, finely divided metal and metal oxides with and without surface treatments.

Component (C):

Component (C) comprises a polyorganosiloxane having the average compositional formula:

$$R^{26}{}_n R^{27}{}_o (OH)_p SiO_{(4-n-o-p)/2}$$

$R^{26}$ is $C_{2-20}$ alkenyl that is directly bonded to silicone and can be exemplified by vinyl, allyl, butenyl, hexenyl and decenyl, $R^{27}$ is a group selected from unsubstituted or substituted monovalent hydrocarbyl (excluding alkenyl), epoxy, cycloepoxy, alkoxy, cylcloalkyl and aryl. The unsubstituted or substituted monovalent hydrocarbyl (excluding alkenyl) can be exemplified by alkyl such as methyl, ethyl, propyl and cyclohexyl, aryl such as phenyl, tolyl and napthyl; haloalkyl such as 3-chloropropyl, 3,3,3,-trifluoropropyl and 2-(nonafluorobutyl)ethyl; and aralkyl such as ethylbenzyl and 1-phenylethyl. The alkoxy can be exemplified by methoxy, ethoxy, n-propoxy and i-propoxy, wherein methoxy and ethoxy are preferred, and n, o, p are positive numbers with n+o+p=1 to 2, n is greater than or equal to 0, p is greater than or equal to 0 and that contains at least alkenyl, hydroxyl, epoxy, cycloepoxy directly bonded to silicon.

Component (D):

Component (D) comprises an organohydrogenoligosiloxane or organohydrogenpolysiloxane that has the average compositional formula $$H_q R^{28}{}_r SiO_{(4-q-r)/2}$$

$R^{28}$ is a group selected from unsubstituted or substituted monovalent hydrocarbyl (excluding alkenyl), preferably selected from alkyl radicals of 1 to 60 carbon atoms such as methyl, ethyl, propyl, butyl, pentyl, n-pentyl, isopentyl, hexyl, and octyl; mononuclear aryl radicals such as phenyl, methylphenyl, cycloalkyl radicals such as cyclohexyl, and haloalkyl radicals, q is greater than 0, r is greater than or equal to 0 and q+r is less than or equal to 3. The organohydrogensiloxane is a necessary component of the curable composition. When the silicone ionomer possesses vinyl or hydride groups, it is required in amounts sufficient to provide an appropriate crosslink density as suitable for the application. When the silicone ionomer or the component (C) as described above possesses epoxy groups, only trace quantities of the organohydrogensiloxane are required as an initiator.

Component (E):

Component (E) comprises an effective amount of transition metal catalyst for facilitating an addition cure hydrosilylation reaction between said vinyl functional cross-linking agents, functional polyorganosiloxane ionomer, and the said hydrogen functional siloxane either by thermal energy or by actinic radiation. To induce the addition reaction between the alkenyl in component (A), (C) and silicone bonded hydrogen in component (D), i.e., hydrosilylation reaction, a transition metal catalyst is required. Further, when the substituents of components (A) and/or (C) are epoxy or cycloepoxy groups, the metal catalyst, in presence of a silicone-hydride initiator, can also facilitate a ring opening polymerization of the epoxy groups. The catalyst can be exemplified by platinum catalyst such as platinic chloride, chloroplatinic acid, bis(acetylacetonato)platinum, and by platinum group metal catalysts such as palladium and rhodium catalysts as well as iron based catalysts. Preferably, the catalyst is platinum, and even more preferably, the platinum catalyst is present in a soluble complex form: $(\eta^5$-Cyclopentadienyl)trialkylplatinum complexes, Pt triazenido complex, $Pt(PPh_3)_2Cl_2$ and the type can be used for the photochemically induced addition reaction. The catalyst can be homogenous or heterogenous catalyst system.

Component (F):

Optional component (F) comprises an additional component selected from UV stabilizer, chain extenders, initiators, cure accelerator, cure inhibitor, pigment, dye, antimicrobial agent, antifungal agent, drug, biocide, surfactant, conductive filler, non-reinforcing fillers such as finely divided surface treated/untreated metal oxides (e.g., titania, zirconia, ceria etc), nanofillers, clay, plasticizers, tackifiers, mold release agents, adhesion promoters, compatibilizers, pharmaceutical excipients, surfactants, compatibilizing agents, radio-opaque substances, antistat agent.

The present invention on the curable ionic silicone composition is based on the functional groups of the ionic silicones that can undergo addition curing either thermally or under actinic radiation to provide transparent to translucent elastomers and gels with excellent physical properties such as tensile strength, hardness, tear strength, modulus, customizable tack and adhesive behavior, permeability to water vapor, and the ability to deliver active ingredients. The elastomers can be liquid silicone rubbers, heat cured elastomers of the type. The gels can be room temperature curable (RTV) or UV cured gels.

The curable silicone compositions produced according to the invention are suitable for many applications in which the known advantageous properties of the silicones and the properties that could be derived from the ionic groups in the silicone ionomers are important, preferably in the fields of personal care applications such as gels, emulsions, healthcare applications, household applications, apparel, sporting goods such as diving masks, paints, coatings, fuel cell, electronic and electro-optic applications, agriculture, membranes, injection moldable and compression moldable rubbers and plastics, and various silicone based rubbers, production of domestic appliances, machine and instrument construction, coatings such as release coatings, protective coatings, anti-fouling coatings, and consumer goods. As a specific example, in the healthcare field, silicone elastomers are used for the fabrication of wound dressings, dressings for scar reduction, drug delivery devices, medical tubing, clinical surfaces, pacemaker leads, pressure sensitive adhesives, wound healing patches, wound management device, medical adhesives, catheters, shunts, valves, stents, transdermal iontophoresis patches, scaffold for tissue engineering, anti-microbial devices, ophthalmic devices, bioinserts, plugs, surgical devices, medical devices, devices for medical storage, childcare products, assisted breathing apparatus, prostheses, reconstructive devices and body implants.

In such a scenario, the presence of micro-organisms such as bacteria, fungi, viruses on the elastomer part can lead to infection and subsequent death or disability of the subject. It is therefore desired that the silicone elastomer has an antimicrobial property.

The curable compositions of the present invention can be rendered antimicrobial via contact with an antimicrobial agent exemplified by but not limited to silver, copper, zinc, chlorhexidine, benzalkonium chloride, biguanide, polyquaternary ammonium compounds, polyquaternary phosphonium compounds, chitosan and its derivatives, antimicrobial peptides such as but not limited to nisin, pediocin, gomesin, pleuricidin and their derivatives and their recombinant forms which can bind to the ionic groups present on the silicone ionomers of the present invention.

Such microbiocides can be released upon contact with physiological or clinical environments and create a transient or permanent antimicrobial effect at the contact site.

In yet another example, addition cured pressure sensitive silicone adhesives are used for the attachment of wound dressings to the periwound skin. Silicones do not stick to the wound bed, but adhere to the skin. Hence they can be removed or repositioned atraumatically.

However, silicone adhesives have low permeability to moisture, and therefore cannot provide an optimally moist environment for enhanced wound healing. The incorporation of ionic groups into such adhesives, as described in the present invention, can lead to an increased hydrophilicity of the adhesive, thereby increasing its moisture permeability.

Additional examples of the industrial utility of the present invention and its reduction to practice are stated as below.

PREPARATIVE EXAMPLES

Example 1

Sulfonic Acid Functionalized Tetramethyldisiloxane

A three necked 500 mL flask was charged with 18.16 g (154.0 mmol) alpha-methylstyrene and 27.2×10-5 g platinum catalyst. The temperature of the resulting mixture was brought to 115 degrees Celsius, then 9.40 g (70.0 mmol) of 1,1,3,3-tetramethyldisiloxane was added dropwise and continued to stir until completion of the hydrosilylation reaction. The complete hydrosilylation was indicated by the disappearance of silicon hydride peak in the $^1$H NMR. The resulting mixture was vacuum stripped to remove unreacted alphamethylstyrene by placing on an oil bath at 150 degrees Celsius for 2 h which gave 23.2 g of aralkylene substituted disiloxane. (Yield: 90%)

To this aralkylene substituted disiloxane (23.2 g, 62.4 mmol), 29.6 g (252.8 mmol) of chlorosulfonic acid was added drop wise through a period of 30 minutes while the mixture being stirred at room temperature. The resulting mixture was continually stirred for an additional 30 minutes. The completion of the reaction was determined by $^1$H NMR where total sulfonation of the aromatic ring was indicated by the disappearance of para-substituted aromatic proton peak. The vacuum stripping of the reaction mixture at low pressure afforded 33.0 g of the sulfonated disiloxane. The NMR analysis of the product indicated the product formation.

Example 2

Sulfonic Acid Functionalized Tetramethyltetracyclosiloxane

A three necked 500 mL flask was charged with 70.08 g (60.0 mmol) alpha-methylstyrene and 10.0×10$^{-4}$ g platinum catalyst. The temperature of the resulting mixture was brought to 115 degrees Celsius, then 30.0 g (120.5 mmol) of 1,3,5,7-tetramethylcyclotetrasiloxane was added drop wise with continued stirring. The progress of the reaction mixture was monitored by $^1$H NMR. After 12 h of the reaction, complete conversion of silicone hydride was indicated by the NMR. Then, the reaction mixture was vacuum stripped at 150 degrees Celsius for 2 h to remove unreacted alpha-methylstyrene which gave 80.5 g aralkylene substituted cyclotetrasiloxane. (Yield: (95%))

To 14.24 g (20.0 mmol) of the above aralkylene substituted cyclotetrasiloxane, 18.64 g (160.0 mmol) of chlorosulfonic acid dissolved in 4.0 mL dichloromethane was added drop wise through a period of 30 minutes while the mixture being stirred at room temperature. The resulting mixture was continually stirred for an additional 30 minutes. The completion of the reaction was indicated by $^1$H NMR where complete sulfonation of the aromatic ring was indicated by the disappearance of para-substituted aromatic proton peak. The vacuum stripping of the reaction mixture at low pressure afforded 20.6 g of the sulfonic acid functional cyclotetrasiloxane as brown viscous gum. $^1$H NMR and $^{29}$Si NMR confirmed the product formation.

Example 3

Sulfonate Functional Polyorganosiloxane Bearing Terminal Hydride Groups

To the sulfonic acid functional cyclotetrasiloxane 20.6 g (20.0 mmol) obtained in Example 2, 587.26 g (1980.0 mmol) of octamethyltetracyclosiloxane and 3.54 g (26.4 mmol) of 1,1,3,3-tetramethyldisiloxane were added and stirred at room temperature. After reaching an equilibrium of ~87 wt % of the linear siloxanes, the reaction mixture was neutralized using 26.9 (320.0 mmol) of moistened sodium bicarbonate at 70 degrees Celsius. The vacuum stripping of the reaction mixture at low pressure provided 542.0 g (85%) of the product as viscous gum. The NMR analysis of the product indicated that the polymer is hydride-terminated sulfonated polydimethylsiloxane Example 4

Sulfonate Functional Polyorganosiloxane Bearing Pendant Hydride Groups

To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,4,7-tetramethyldisiloxane were added and stirred at room temperature. After reaching an equilibrium of ~87 wt % of the linear siloxanes, the reaction mixture was neutralized using 21.23 g (506.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sulfonated polydimethylsiloxane bearing pendant hydride groups.

Example 5

Sulfonate Functional Polyorganosiloxane Bearing Terminal Vinyl Groups

To the sulfonic acid functional cyclotetrasiloxane 5.7 g (8.0 mmol) obtained in Example 2, 474.7 g (1600.0 mmol) of octamethyltetracyclosiloxane and 1.48 g (8.0 mmol) of 1,1,3,3-tetramethyl-1,3-divinyldisiloxane were added and continually stirred at room temperature. After reaching equilibrium of ~87 wt % of the linear siloxanes, the reaction mixture was neutralized using 10.0 g (128.0 mmol) moistened sodium bicarbonate at 70 degrees Celsius. The vacuum stripping of the reaction mixture at low pressure afforded 411.0 g of the product as viscous gum. The NMR analysis of the product indicated that the polymer is vinyl-terminated sulfonated polydimethylsiloxane. (Yield: 84%).

To the sulfonic acid functional polydimethylsiloxane 10.00 g (0.3 mmol) obtained from above, 0.28 g (1.2 mmol) of moistened silver oxide was added and continually stirred at 70 degrees Celsius for 6 h when the silver salt of sulfonic acid functional polydimethylsiloxane bearing terminal vinyl groups was obtained as viscous gum. The polymer had a viscosity of 55.8 Pa-s at a shear rate of 10 rad/s when measured by a HAAKE Rheometer at 20 degrees Celsius.

Similarly, the $Na^+$, $Ca^{2+}$, $Mg^{2+}$, $Al^{3+}$, $Zn^{2+}$, $Co^{2+}$ salts of sulfonic acid functional polyorganosiloxanes have been synthesized using the respective oxides. Also, organic cations like chlorhexidine and biguanide have been synthesized using their respective salt solutions.

Example 6

Sulfonate Functional Polyorganosiloxane Bearing Pendant Vinyl Groups

To the sulfonic acid functional disiloxane 4.17 g (7.9 mmol) obtained in Example 1, 234.3 g (790.0 mmol) of octamethyltetracyclosiloxane and 5.4 g (15.8 mmol) of 1,3,5,7-tetramethyl-1,3,5,7 tetravinylcyclotetrasiloxane were added and continually stirred at room temperature. After reaching an equilibrium of ~87% the reaction mixture was neutralized using 5.3 (63.0 mmol) moistened sodium bicarbonate at 70 degrees Celsius. The vacuum stripping of the reaction mixture at low pressure afforded 215.0 g of the product as viscous gum. The NMR analysis of the product indicated that the polymer is a sulfonated polydimethylsiloxane bearing pendant vinyl groups.

Addition Cure Formulations:

Incorporation of the sulfonate functional polyorganosiloxanes of Examples 3-6 in elastomer based formulations:

Example 7A

Formulation by Blending

The sulfonate functional polyorganosiloxane bearing terminal hydride groups (Example 3)(25 g) was mixed with the commercially available elastomer formulation that is a Liquid silicone rubber (LSR 2050 Parts A and B, Momentive) (50 g) in a blender.

Example 7B

Formulation by Blending

The sulfonate functional polyorganosiloxane bearing terminal vinyl groups (Example 5) (25 g) was mixed with the elastomer (Liquid silicone rubber 2050 Parts A and B) (50 g) in a blender.

Example 8A

In Situ Addition Cure Liquid Silicone Rubber Formulation

The sulfonate functional polyorganosiloxane (Example 5) (66 g) was mixed with the fumed silica (50.35 g) from Evonic, Hexamethyldisilazane (10.9 g), water (4.98 g) and the vinyl PDMS of viscosity ~1 Pa·s (U1, Momentive) (67.39 g) in a Ross Mixer and heated to 120 degrees Celsius under vacuum.

Example 8B

In Situ Addition Cure Liquid Silicone Rubber Formulation

The sulfonate functional polyorganosiloxane (Example 5) (134 g) was mixed with the functionalized fumed silica (50.35 g) from Evonic, Hexamethyldisilazane (10.9 g), and water (4.98 g) in a Ross Mixer and heated to 120 degrees Celsius under vacuum.

Example 8C

In Situ Addition Cure Liquid Silicone Rubber Formulation

The sulfonate functional polyorganosiloxane (Example 5) (66 g) was mixed with the sol gel nanosilica (312.5 g) in isopropanol (16% solid content), U65 vinyl functional siloxane (25 g) from Momentive and U10 vinyl functional siloxane (59 g) from Momentive in a Ross Mixer and heated to 120 degrees Celsius under vacuum.

The rheology data of the sulfonate functional polyorganosiloxanes blended with formulated in functional PDMS and the control example (LSR 2050) was determined by their viscosity (Pa·s) as given in Table 1.

TABLE 1

| Examples | Viscosity (Pa · S) |
|---|---|
| Comparative example (LSR 2050) | 587 |
| Example 7b | 1129 |
| Example 8a | 3222 |
| Example 8b | 8975 |
| Example 8c | 830 |

Curing:
Platinum Catalyzed Thermal Curing:

Example 9A

50 Grams of the formulation in Example 7a were cured by compression molding at 180 degrees Celsius for 10 min under pressure to get an elastomeric sheet.

Example 9B

50 Grams of the formulation in Example 7b were cured by compression molding at 180 degrees Celsius for 10 min under pressure to get an elastomeric sheet.

Example 10A

50 Grams of the formulation in Example 8a were mixed with the platinum catalyst, hydride crosslinker (Vern-730, Momentive), inhibitor and cured by compression molding at 180 degrees Celsius for 10 min under pressure to get an elastomeric sheet.

Example 10B

50 Grams of the formulation in Example 8b were mixed with the platinum catalyst, hydride crosslinker (Vern-730, Momentive Performance Materials), inhibitor and cured by compression molding at 180 degrees Celsius for 10 min under pressure to get an elastomeric sheet.

Example 10C

50 Grams of the formulation in Example 8c were mixed with the platinum catalyst, hydride crosslinker (Vern-730, Momentive Performance Materials), inhibitor and cured by compression molding at 180 degrees Celsius for 10 min under pressure to get an elastomeric sheet.

Platinum Catalyzed UV Curing:

Example 10D

50 Grams of the formulation in Example 8a were mixed with the platinum catalyst [Trimethyl(methylcyclopentadienyl)platinum(IV) (STREM Chemicals)], hydride crosslinker (Vern-730, Momentive), inhibitor and cured by UV at 2000 mW/cm$^2$ for 200 seconds The physical properties and the transparency data were determined and the values are given in Table 2. The cure kinetics data for the fumed silica and nano silica loaded examples are given in Table 3.

TABLE 2

| Example | Transparency % | Haze % | Tensile strength MPa | % strain | Hardness (Shore A) | Water uptake (24 hrs at 35° C.) % |
|---|---|---|---|---|---|---|
| Control LSR2050 | 90.1 | 11.7 | 9.00 | 600 | 50 | <5 |
| 9a | 82.2 | 30.1 | 2.50 | 411 | 43 | 27 |
| 9b | 83.7 | 24.4 | 2.89 | 332 | 45 | 30 |
| 10a | 77.7 | 44.6 | 6.08 | 362 | 53 | 35 |
| 10b | 76.5 | 56.2 | 3.82 | 123 | 55 | 32 |
| 10c | 80 | 20 | 6.17 | 378 | 47 | 32 |

TABLE 3

| Example | T60 (min) |
|---|---|
| LSR control | 2.03 |
| Example 8a | 2.13 |
| Example 8c | 3.62 |

Actives Loading:

Example 11

Loading of Silver

The elastomer of example 10a was soaked in 0.1M aqueous silver nitrate solution for half an hour in a brown glass bottle in a dark cabinet. Then the sample was rinsed with DI water allowed to dry and then analyzed for the presence of silver through SEM and EDX experiments. There is minimal change in the color of the elastomer on silver loading. The change in the color is measure by the L*a*b* measurements in the reflectance mode on exposure to air and heating at 200 degree Celsius for 20 days and is represented in Table 4. The theoretical loading of the silver in the elastomer samples are also shown in the Table 5.

TABLE 4

| Example 10a | L* | a* | b* |
|---|---|---|---|
| Day 1 | 82.65 | 0 | 7.15 |
| Day 20 | 81.45 | 0.5 | 10.28 |

TABLE 5

| Examples | Theoretical Ag loading (ppm) |
|---|---|
| Comparative example (LSR 2050) | 0 |
| Example 9a | 2300 |
| Example 9b | 2300 |
| Example 10a | 2300 |
| Example 10b | 6600 |

Example 12

Controlled Release of Silver

The silver loaded elastomeric film of Example 11 was dried and immersed in 50 mL of 0.01M aqueous NaNO$_3$ solution at pH 7. At regular intervals, 20 mL of the solution was withdrawn and replaced by NaNO$_3$ solution to study the cumulative release of silver by Inductively coupled plasma analysis. This was done for over a period of 120 hrs. FIG. 1 shows the release of silver from the Example 10a with time and this follows a controlled release pattern with an initial burst of silver.

Example 13

Formulation of Room Temperature Curable Gels

Varying amounts of the sulfonate functional polydiorganosiloxane bearing terminal vinyl groups (as Example 5,) were blended with vinyl-terminated PDMS (U1, 1 Pa·s viscosity, Momentive Performance Materials), hydride-functional PDMS crosslinker (Vern 230, Momentive), and hydride terminated PDMS chain extender (TP 3359, Momentive Performance Materials) inhibitor (1,1,3,3-tetramethyl-1,3-divinyldisiloxane, MviMvi) and blended in a high speed mixer. Platinum catalyst was added to this mixture and it was poured in suitable polystyrene molds or drawn as a thin film on a PET substrate followed by curing at room temperature. Upon curing, a soft, tacky composition was obtained. The crosslinker and chain extender content was varied such that the ratio of silicone hydride groups to vinyl silicone groups ranged from 0.477 to 1 (Example 13a to 13c), which gives compositions with varying softness and tack (Table 6).

TABLE 6

Sulfonate functional silicone gels

| Component (gm) | Control | Example 13a 25/75 Ex. 5/U1 | Example 13b 50/50 Ex. 5/U1 | Example 13c 90/10 Ex. 5/U1 |
|---|---|---|---|---|
| U1 | 23.809 | 17.857 | 11.905 | 2.380 |
| Vinyl-functional sulfonated silicone | 0 | 5.952 | 11.905 | 21.428 |
| Pt-D | 0.006 | 0.006 | 0.0125 | 0.035 |
| MviMvi | 0.001 | 0 | 0 | 0.001 |
| Vern 230 | 0.375 | 0.293 | 0.211 | 0.244 |
| TP 3359 | 0.407 | 0.407 | 0.407 | 0.5 |
| SiH/ViSi ratio | 0.477 | 0.477 | 0.477 | 0.8 |

Example 14

Water Uptake of Room Temperature Curable Gels

Figure 2:
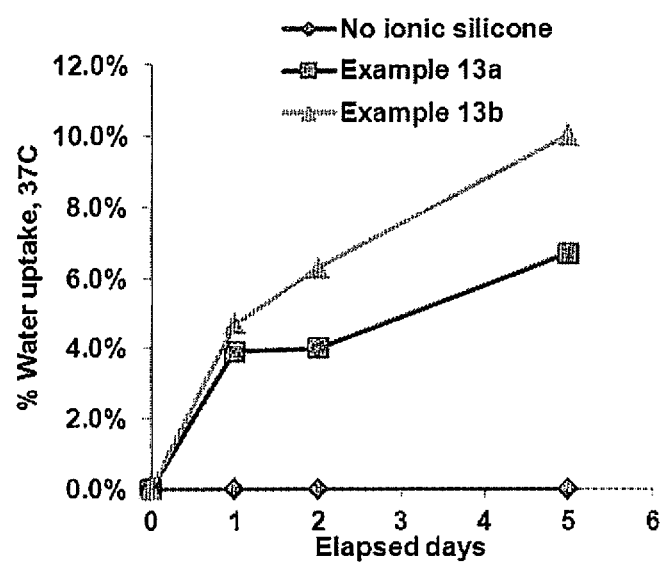
FIGS. 2 and 3 are graphs showing water uptake of addition cure silicone gels containing an ionic silicone with sulfonate groups.
Figure 3:
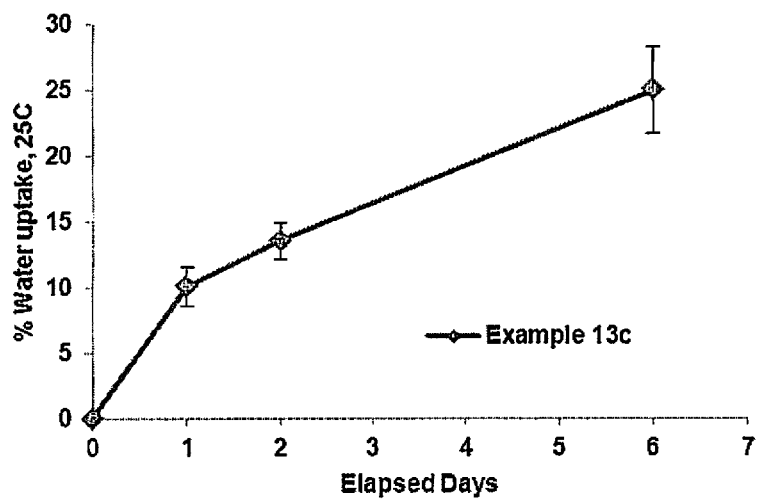

The silicone ionomer containing gels Control, Example 13a and Example 13b were weighed and incubated in simulated wound fluid (142 mM NaCl, 2.5 mM $CaCl_2$, 2 mM $H_2O$ in DI water) at 37 degrees Celsius, as per the British Standard BS EN 13726-1:2002 (Test methods for primary wound dressings—Part 1: Aspects of absorbency). The gel of Example 13c was incubated in DI water at ambient temperature. At varying time intervals, the gel samples were blotted dry and weighed. The percentage increase in weight, corresponding to imbibition of water by the gels, was calculated as water uptake. The water uptake by the gels was found to be proportional to their silicone ionomer content, and progressively increased with the incubation period (FIGS. 2 and 3).

Example 15

Tack Measurement of Room Temperature Curable Gels

The silicone ionomer containing gels Control, Example 13a and Example 13b were cast as circular sheets of 2 mm thickness and 60 mm diameter in polystyrene molds. Upon curing, the sheets were post-cured at 50 degree Celsius for 2 h, removed and the tack was measured using a Dia-Stron Miniature tensile tester (MTT 175) equipped with the parallel plate attachment. Briefly, the gel sheet occupied the lower stainless steel plate, which is connected to the force transducer of the instrument. The upper plate was fixed to the instrument's force arm, aligned, and used to press the gel sheet at a load of 50 g for 20 seconds, following which it was pulled upwards at a rate of 100 mm/min. The amount of force required to separate the top plate from the gel was measured by the force transducer as a function of separation distance, and the peak value encountered is reported as tack force. The test was repeated for twenty cycles per sample, and each gel sample was tested in duplicate. It was found that a statistically significant reduction of tack occurred upon the incorporation of silicone ionomers within the gels (Table 7).

TABLE 7

Peak tack force measurement of sulfonate functional silicone gels

| Formulation | Peak tack force ($gm_f$) |
| --- | --- |
| Control | 308 ± 30 |
| Example 13a | 290 ± 39 |
|  | (p < 0.05 vs control) |
| Example 13b | 250 ± 12 |
|  | (p < 0.05 vs control |
|  | p > 0.05 vs 25%) |

Example 16

Measurement of Moisture Vapor Transport of Room Temperature Curable Gels

The moisture vapor transport property of the silicone ionomer containing gels was measured as per the British Standard BS EN 13726-1:2002 (Test methods for primary wound dressings—Part 1: Aspects of absorbency). The gel samples control, and example 13b were used in form of circular sheets of 2 mm thickness and were prepared as per the following table (Table 8):

TABLE 8

|  |  | Ionic Silicone gel 50/50 |
| --- | --- | --- |
| Component (gm) | Control | Ex 5/U1 |
| U1 | 23.809 | 11.905 |
| Vinyl-functional sulfonated silicone | 0 | 11.905 |
| Pt-D | 0.0125 | 0.0125 |
| MviMvi | 0.01 | 0.01 |
| Vern 230 | 0.463 | 0.291 |
| TP 3359 | 0.304 | 0.304 |
| SiH/ViSi ratio | 0.5 | 0.5 |

Figure 4:
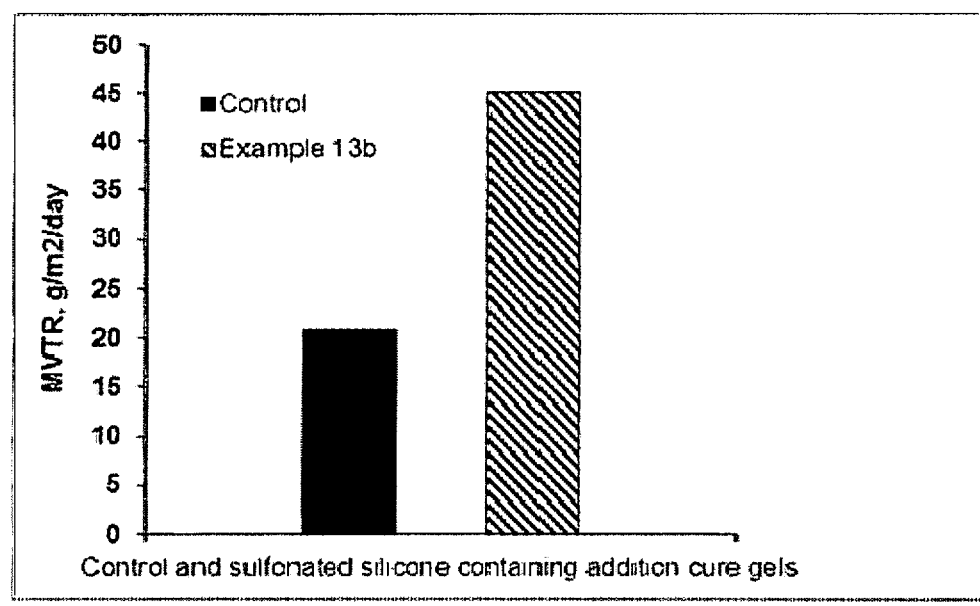
FIG. 4 is a graph showing moisture vapor transport rate (MVTR) of silicone gel containing an ionic silicone with sulfonate groups.

An apparatus similar to the Paddington Cups (Surgical Materials Testing Laboratory, Cardiff, UK) were used. The apparatus consists of an aluminum cup open at both ends. The gel samples were clamped on one end of the cup using an aluminum flange with a known orifice area. The cup was filled with a known quantity of DI water and the remaining end was closed with a blind flange. Vacuum grease was applied at all flange connections to prevent moisture loss. The closed assembly was weighed and placed in an 'Inverted position' (water in contact with the affixed gel sheet), in a constant temperature (25 degrees Celsius) and humidity (50% RH) environment. Periodically the assembly was weighed and any loss in weight was attributed to the transport of water vapor through the gel sheet. The average daily water vapor loss (in $g/m^2/day$) was estimated from the slope of the weight loss vs. time elapsed curve. Each gel formulation was tested in triplicate (FIG. 4).

Example 17

UV Curable Addition Cure Silicone Adhesive

An addition cure silicone adhesive composition was prepared as per the following Table (Table 9):

TABLE 9

| Component | Weight (gm) |
| --- | --- |
| Vinyl-functional sulfonated silicone | 5.0 |
| MGT 2364 | 0.150 |
| Divinyl dimethyl siloxane | 0.02 |
| Vern 140 | 0.1 |
| TP 3359 | 0.370 |
| SiH/ViSi ratio | 4.06 |

The components were mixed together and the UV-activated addition cure catalyst Trimethyl($\eta^5$-methylcyclopentadienyl)platinum(IV) (STREM Chemicals) was added to the mixture. The mixture was then irradiated with UV-light of 320 nm wavelength (105 $mW/cm^2$) for 90 seconds, which resulted in complete curing of the mixture to result in a tacky adhesive.

Example 18

Preparation of Ionic Silicone Masterbatches Containing Antimicrobials and Gels Thereof Vinyl functional sulfonated silicone prepared as described was dissolved in hexane. This solution was contacted with 20% solution of chlorhexidine gluconate, or 1M $CuSO_4$ to exchange the sodium ions with chlorhexidine or copper respectively. After 48 h contact time, the silicone containing organic phase was separated and washed with a 1:1 solution of methanol and water several times, to remove nonspecifically bound copper and chlorhexidine gluconate. The organic phase was dried in a rotary evaporator to remove water and residual solvents.

Adhesive formulations were prepared from the masterbatches using the following components in quantities described as below (Table 10):

TABLE 10

| Component | Weight (gm) |
|---|---|
| Vinyl-functional sulfonated silicone | 2.5 |
| MGT 2364 | 0.15 |
| Sulfonated silicone antimicrobial masterbatch | 2.5 |
| Vern 140 | 0.10 |
| TP 3359 | 0.37 |
| SiH/ViSi ratio | 2.07 |

To this mixture, UV-cure Pt catalystTrimethyl($\eta^5$-methylcyclopentadienyl)platinum(IV) (STREM Chemicals) was added and the mixture was cast on a PET sheet and cured using UV radiation at 105 mW/cm². The cured samples were analyzed for chlorhexidine content by estimation of nitrogen using C/H/N analysis. Copper content was estimated by digesting the adhesive using HF and analyzing the digest using ICP Inductively Coupled Plasma. A chlorhexidine content of 2.5% and a copper content of 1% w/w was obtained using these techniques.

Figure 5:
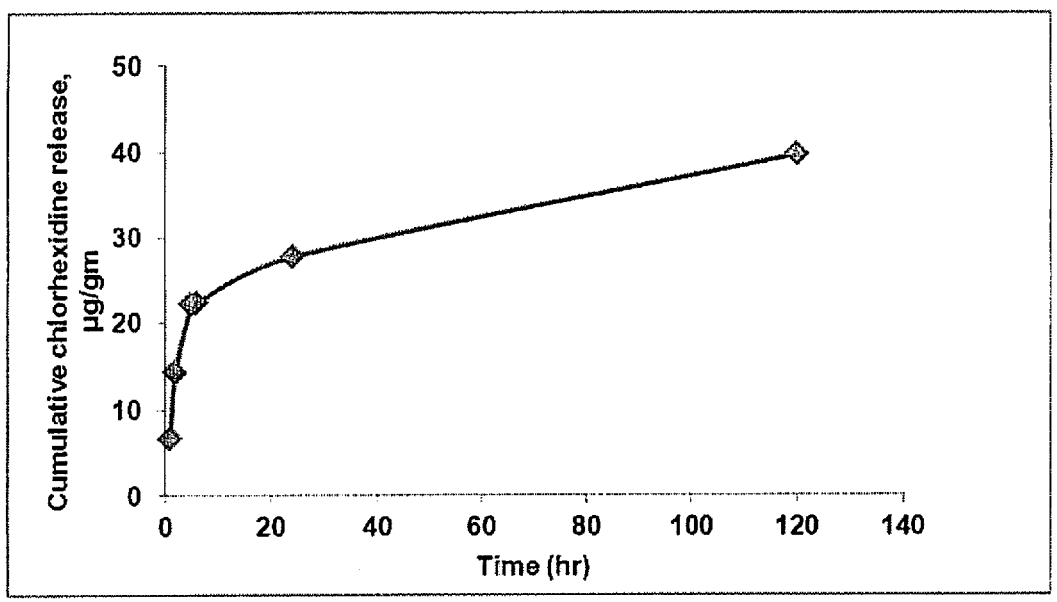
FIG. 5 is a graph showing cumulative release of chlorhexidine from a silicone gel containing an ionic silicone with sulfonate groups.

The cured adhesives were tested for release of antimicrobials by immersing in solutions of suitable counterions. Chlorhexidine gluconate release was performed in 50 mM phosphate buffer, and copper release was done in 0.1M NaNO₃ solution. No copper ions were observed in the aliquots, whereas a sustained release of chlorhexidine digluconate was observed (FIG. 5).

Example 19

Antimicrobial Adhesive Based on Sulfonated Silicone Masterbatch of Poly(Hexamethylene) Biguanide A sulfonated silicone masterbatch was prepared as described in Example 18, except that the antimicrobial was a 10% aqueous solution of pol(hexamethylene) biguanide (PHMB) (Arch Biocides). The adhesive formulation consisted of the following components shown in Table 11:

TABLE 11

| Component | Weight (gm) |
|---|---|
| Vinyl-functional sulfonated silicone | 2.5 |
| MGT 2364 | 0.169 |
| Sulfonated silicone antimicrobial masterbatch | 2.5 |
| Vern 140 | 0.154 |
| TP 3359 | 0.383 |
| SiH/viSi ratio | 2.07 |

To this, the UV-cure Platinum catalyst Trimethyl($\eta^5$-methylcyclopentadienyl) platinum(IV) (STREM Chemicals) was added. The formulation was cast on PET sheet and cured under UV radiation (105 mW/cm2) to yield a translucent adhesive film. The adhesive was subjected to C/H/N analysis to determine PHMB content, and a loading of 0.2% w/w nitrogen, corresponding to ppm of PHMB was obtained.

Example 20

Ionic Silicone Containing Peroxide-Cured Silicone Rubber

Vinyl-functional sulfonated silicone (Example 5) was blended at a loading of 50% by weight into a general purpose high consistency rubber (HCR) formulation TSE 221-5U from Momentive Performance Materials. In addition to the inherently present filler, varying amounts of nanoclay (Cloisite 30B) were added to the formulation. The formulation was compression molded at a temperature of 180 degrees Celsius by use of a proprietary mixture of peroxide thermal initiators. The resulting rubber sheets were evaluated for mechanical properties and hardness and the following results were obtained (Table 12).

TABLE 12

| Formulation | Tensile Strength (MPa) | % Strain | Modulus @ 100% strain | Hardness Shore A |
|---|---|---|---|---|
| HCR + 50% ionic silicone | 4.7 | 325.1 | 1.89 | 43 |
| HCR + 50% ionic silicone + 2.5% clay | 5.7 | 311 | 2.44 | 53 |
| HCR + 50% ionic silicone + 5% clay | 5.6 | 324.6 | 2.551 | 53 |

While the above description contains many specifics, these specifics should not be construed as limitations of the invention, but merely as exemplifications of preferred embodiments thereof. Those skilled in the art will envision many other embodiments within the scope and spirit of the invention as defined by the claims appended hereto.

What is claimed is:

1. A curable composition containing an ionic silicone of the following formula (I):

$$M^1{}_a M^2{}_b M^3{}_c D^1{}_d D^2{}_e D^3{}_f T^1{}_g T^2{}_h T^3{}_i Q_j \qquad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$.

wherein $R^1$, $R^2$, $R^5$, $R^6$, $R^8$, $R^9$, $R^{11}$, $R^{13}$, and $R^{15}$ are aliphatic, aromatic or fluoro monovalent hydrocarbons having from 1 to 60 carbon atoms, $R^3$, $R^{10}$, $R^{16}$ are independently chosen from —CH₂CH(R')(C$_n$H$_{2n}$)—O—(C₂H₄O)$_o$—(C₃H₆O)$_p$—(C₄H₈O)$_q$—R', wherein subscript n is zero or positive and has a value in the range of 0 to 6, subscripts o, p and q are zero or positive and independently selected from a value in the range of 0 to 100, subject to the limitation of o+p+q greater than or equal to 1, wherein R' is hydrogen or an aliphatic, aromatic or fluoro hydrocarbon having from 1 to 60 carbon atoms, $R^4$, $R^{12}$, $R^{17}$ are monovalent radical-bearing ion-pairs having the formula (II) or zwitterions having formula (III), wherein formula (II) is as follows, $$\text{-A-I}^{x-} M_n{}^{y+} \qquad (II);$$

where
- A is a spacing group having at least one spacing atoms selected from a divalent hydrocarbon or hydrocarbonoxy group,
- I is an ionic group selected from sulfonate —SO$_3^-$, sulfate —OSO$_3^-$, carboxylate —COO$^-$, phosphonate —PO$_3^{2-}$ and phosphate —OPO$_3^{2-}$ groups,
- M is hydrogen or a cation independently selected from alkali metals, alkaline earth metals, transition metals, metal complexes, quaternary ammonium and phosphonium groups, cationic hydrocarbons, organic cations, alkyl cations, cationic biopolymers, and the zwitterions have the formula (III):

—R'—NR''$_2^+$—R'''—I      (III)

where
- R' is a divalent hydrocarbon radical containing from 1 to about 60 carbon atoms,
- R'' is monovalent hydrocarbon radical containing from 1 to about 60 carbon atoms,
- R''' is divalent hydrocarbon radical containing from 2 to about 20 carbon atoms, specifically from 2 to about 8 carbon atoms and more specifically from 2 to about 4 carbon atoms; and,
- I is an ionic group selected from sulfonate —SO$_3^-$, sulfate —OSO$_3^-$, carboxylate —COO$^-$, phosphonate —PO$_3^{2-}$ and phosphate —OPO$_3^{2-}$ groups,
- where R$^7$, R$^{14}$, and R$^{18}$ are independently selected from hydrogen, or unsaturated monovalent radicals or epoxy group containing radicals, where
- the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than zero, and c+f+i is greater than zero, a+d+g is greater than zero, and a+b+c is greater than zero with the proviso that h+I is greater than zero.

2. The composition of claim 1 wherein R$^4$, R$^{12}$, R$^{17}$ are monovalent radical-bearing ion-pairs having the formula (II) and the divalent group of A in formula (II) is an arylene group selected from the group consisting of —(CH$_2$)$_k$C$_6$H$_4$(CH$_2$)$_k$—, —CH$_2$CH(CH$_3$)(CH$_2$)$_k$C$_6$H$_4$—, and —CH$_2$CH(R$^1$)(CH$_2$)$_l$C$_6$H$_3$R$^{19}$ where R$^1$ is as defined, R$^{19}$ is a monovalent radical of from about 1 to about 20 carbon atoms, a sulfur atom(s), nitrogen atom(s), oxygen atom(s) or a radical containing combinations of the above atoms, where l has a value of 0 to 20, and k has a value of 0 to 20.

3. The composition of claim 1 wherein R$^4$, R$^{12}$, R$^{17}$ are monovalent radical-bearing ion-pairs having the formula (II) and the divalent group of A in formula (II) is an alkylene group of the formula —(CHR$^{20}$)$_m$— where m has a value of 1 to 20 and R$^{20}$ is hydrogen or R$^1$.

4. The composition of claim 1 wherein R$^4$, R$^{12}$, R$^{17}$ are monovalent radical-bearing ion-pairs having the formula (II) and the divalent group of A in formula (II) is a hydrocarbonoxy group selected from (CHR$^{20}$)$_m$—(O—CH(R$^{20}$)(CH$_2$)$_p$—O—(CH$_2$)$_l$— where l has a value of from 0 to 20, m has a value of 0 to 50 and p has the value from 1 to 50.

5. The composition of claim 1 wherein R$^4$, R$^{12}$, R$^{17}$ are monovalent radical-bearing ion-pairs having the formula (II) and M is a cation independently selected from Li, Na, K, Cs, Mg, Ca, Ba, Zn, Cu, Fe, Ni, Ga, Al, Mn, Cr, Ag, Au, Pt, Pd, Pb, Sb, Ru, Sn Rh, Co, Ce, Eu, Gd and La and R$^7$, R$^{14}$, R$^{18}$ are curable functional groups independently selected from hydrogen or the monovalent radical containing the group of the general formulae

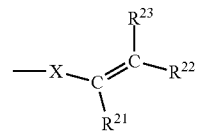  (IV)

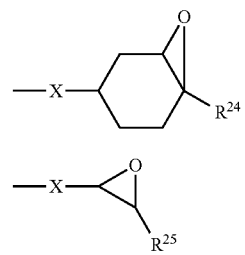  (V)

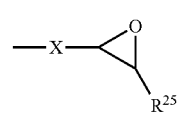  (VI)

wherein R$^{21}$ to R$^{25}$ are independently selected from hydrogen aliphatic/aromatic monovalent hydrocarbon having from 1 to 60 carbon atoms, X is a divalent hydrocarbon linkage consisting of 1 to 60 carbon atoms and 0 to 20 heteroatoms selected from oxygen, nitrogen and sulfur.

6. The composition of claim 1 wherein R$^1$, R$^2$, R$^5$, R$^6$, R$^8$, R$^9$, R$^{11}$, R$^{13}$, and R$^{15}$ are selected from the group consisting of methyl, ethyl, n-propyl, iso-propyl, n-butyl, isobutyl, tert-butyl, n-pentyl, iso-pentyl, neopentyl, tert-pentyl, n-hexyl, n-heptyl, n-octyl, isooctyl, 2,2,4-trimethylpentyl group, n-nonyl group, n-decyl group, cyclopentyl, cyclohexyl, cycloheptyl, methylcyclohexyl, phenyl, naphthyl; o-, m- and p-tolyl, xylyl, ethylphenyl and benzyl.

7. The composition of claim 1 further including 0-99 parts by weight, based on total composition weight, of reinforcing filler or non-reinforcing filler selected from silica, fumed silica, nano silica, functionalized or unfunctionalized silicone resins, natural and synthetic fibers, polysaccharides, cork, graphite and carbon black, graphene, clay, boron nitride, finely divided metal and metal oxides with and without surface treatments.

8. A curable composition containing an ionic silicone of the following formula (I):

M$^1_a$M$^2_b$M$^3_c$D$^1_d$D$^2_e$D$^3_f$T$^1_g$T$^2_h$T$^3_i$Q$_j$   (I)

wherein:
- M$^1$=R$^1$R$^2$R$^3$SiO$_{1/2}$
- M$^2$=R$^4$R$^5$R$^6$SiO$_{1/2}$
- M$^3$=R$^7$R$^8$R$^9$SiO$_{1/2}$
- D$^1$=R$^{10}$R$^{11}$SiO$_{2/2}$
- D$^2$=R$^{12}$R$^{13}$SiO$_{2/2}$
- D$^3$=R$^{14}$R$^{15}$SiO$_{2/2}$
- T$^1$=R$^{16}$SiO$_{3/2}$
- T$^2$=R$^{17}$SiO$_{3/2}$
- T$^3$=R$^{18}$SiO$_{3/2}$
- Q=SiO$_{4/2}$.

wherein R$^1$, R$^2$, R$^5$, R$^6$, R$^8$, R$^9$, R$^{11}$, R$^{13}$, and R$^{15}$ are aliphatic, aromatic or fluoro monovalent hydrocarbons having from 1 to 60 carbon atoms, R$^3$, R$^{10}$, R$^{16}$ are independently chosen from —CH$_2$CH(R')(C$_n$H$_{2n}$)—O—(C$_2$H$_4$O)$_o$—(C$_3$H$_6$O)$_p$—(C$_4$H$_8$O)$_q$—R', wherein subscript n is zero or positive and has a value in the range of 0 to 6, subscripts o, p and q are zero or positive and independently selected from a value in the range of 0 to 100, subject to the limitation of o+p+q greater than or equal to 1, wherein R' is hydrogen or an aliphatic, aromatic or fluoro hydrocarbon having from 1 to 60 carbon atoms, $R^4, R^{12}, R^{17}$ are monovalent radical-bearing ion-pairs having the formula (II) or zwitterions having formula (III), wherein formula (II) is as follows,

where
- A is a spacing group having at least one spacing atoms selected from a divalent hydrocarbon or hydrocarbonoxy group,
- I is an ionic group selected from sulfonate —$SO_3^-$, sulfate —$OSO_3^-$, carboxylate —$COO^-$, phosphonate —$PO_3^{2-}$ and phosphate —$OPO_3^{2-}$ groups,
- M is hydrogen or a cation independently selected from alkali metals, alkaline earth metals, transition metals, metal complexes, quaternary ammonium and phosphonium groups, cationic hydrocarbons, organic cations, alkyl cations, cationic biopolymers, and the zwitterions have the formula (III):

where
- R' is a divalent hydrocarbon radical containing from 1 to about 60 carbon atoms,
- R" is monovalent hydrocarbon radical containing from 1 to about 60 carbon atoms,
- R'" is divalent hydrocarbon radical containing from 2 to about 20 carbon atoms, specifically from 2 to about 8 carbon atoms and more specifically from 2 to about 4 carbon atoms; and,
- I is an ionic group selected from sulfonate —$SO_3^-$, sulfate —$OSO_3^-$, carboxylate —$COO^-$, phosphonate —$PO_3^{2-}$ and phosphate —$OPO_3^{2-}$ groups,
- where $R^7, R^{14}$, and $R^{18}$ are independently selected from hydrogen, or unsaturated monovalent radicals or epoxy group containing radicals, where
the subscript a, b, c, d, e, f, g, h, i, j are zero or positive subject to the following limitations: the sum a+b+c+d+e+f+g+h+i+j is greater than or equal to 2 and less than or equal to 6000, b+e+h is greater than zero, and c+f+i is greater than zero, the composition further including a polyorganosiloxane having the average compositional formula:

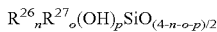

where $R^{26}$ is $C_{2-20}$ alkenyl that is directly bonded to silicone, $R^{27}$ is a group selected from unsubstituted or substituted monovalent hydrocarbyl other than alkenyl, alkoxy, cylcloalkyl, epoxy, cycloepoxy and aryl, and n, o, and p are positive numbers with n+o+p=1 to 2, n is greater than or equal to zero, p is greater than or equal to zero.

9. The composition of claim 8 wherein $R^{26}$ is vinyl, allyl, butenyl, hexenyl or decenyl.

10. The composition of claim 9 wherein $R^{27}$ is a group selected from methyl, ethyl, propyl, cyclohexyl, phenyl, tolyl, napthyl, 3-chloropropyl, 3,3,3,-trifluoropropyl, 2-(nonafluorobutyl)ethyl, ethylbenzyl, 1-phenylethyl, methoxy, ethoxy, n-propoxy and iso-propoxy, epoxy and cycloepoxy.

11. The composition of claim 1 further including organohydrogenoligosiloxane or organohydrogenpolysiloxane that has the average compositional formula

where $R^{28}$ is a group selected from unsubstituted or substituted monovalent hydrocarbyl (excluding alkenyl) selected from alkyl radicals of 1 to 60 carbon atoms, q is greater than zero, r is greater than or equal to zero, and q+r is less than or equal to 3.

12. The composition of claim 11 wherein $R^{28}$ is selected from the group consisting of methyl, ethyl, propyl, butylpentyl, n-pentyl, isopentyl, hexyl, octyl, phenyl, methylphenyl, cyclohexyl and haloalkyl radicals.

13. The composition of claim 1 further comprising a catalyst.

14. The composition of claim 13 wherein the catalyst is a transition metal based catalyst and selected from platinic chloride, chloroplatinic acid, bis(acetylacetonato)platinum, ($\eta^5$-cyclopentadienyl)trialkylplatinum complexes, Pt triazenido complex, $Pt(PPh_3)_2O_2$, iron, palladium and rhodium complexes.

15. The composition of claim 1 further including one or more components selected from UV stabilizer, chain extenders, cure accelerator, cure initiator, cure inhibitor, pigment, dye, antimicrobial agent, antifungal agent, drug, biocide, surfactant, conductive filler, finely divided surface treated/untreated metal oxides, nanofillers, clay, plasticizers, tackifiers, mold release agents, adhesion promoters, compatibilizers, pharmaceutical excipients, surfactants, compatibilizing agents, radio-opaque substances and antistatic agents.

16. A transparent to translucent silicone rubber composition comprising the curable ionic silicone of claim 1.

17. A silicone rubber composition prepared by thermally curing the composition of claim 16 in the presence of a platinum catalyst.

18. A silicone rubber composition prepared by UV curing of the composition of claim 16 in the presence of a platinum catalyst.

19. A silicone rubber composition prepared by thermally curing the composition of claim 16 in the presence of a peroxide initiator.

20. The silicone rubber composition of claim 16 optionally comprising silver, copper, zinc, chlorhexidine, benzalkonium chloride, biguanide, polyquaternary ammonium compounds, quaternary phosphonium compounds, chitosan and its derivatives, antimicrobial peptides selected from nisin, pediocin, gomesin, pleuricidin and derivatives thereof as antimicrobial agents.

21. A transparent to translucent, silicone gel composition comprising the curable ionic silicone of claim 1.

22. A silicone gel composition prepared by thermally curing the composition of claim 21 in the presence of a platinum catalyst.

23. A silicone gel composition prepared by UV curing of the composition of claim 21 in the presence of a UV catalyst.

24. An adhesive composition containing the silicone gel composition of claim 21.

25. The silicone gel composition of claim 21 optionally comprising silver, copper, zinc, chlorhexidine, benzalkonium chloride, biguanide, polyquaternary ammonium compounds, polyquaternary phosphonium compounds, chitosan and its derivatives, antimicrobial peptides selected from nisin, pediocin, gomesin, pleuricidin and their derivatives and recombinant forms as antimicrobial agents.

26. A product for healthcare, personal care, automobile coatings, household paints, laundry detergents, textiles, electronics/electrical, aerospace, membranes, adhesives, fuel cells, construction, apparel, sporting goods, production of domestic appliances, machine and instrument construction and consumer goods said product comprising the composition of claim 1.

27. The healthcare product of claim 26 comprising one or more additional agents selected from the group consisting of metals, metal ions, bioactives, anti-acne agents, anti-ageing agents, anti-caries agents, anti-fungal agents, anti-microbial agents, anti-oxidants, anti-cancer, anti-viral, anti-inflammatory, anti-coagulants, hemostatic agents, exfoliants, hormones, enzymes, medicinal compounds, biocides, external analgesics, oral care agents, oral care drugs, oxidizing agents, reducing agents, skin protectants, essential oils, insect repellents, UV light absorbing agents, solar filters, pigments, hydrating agents, vitamins and combinations thereof.

28. A product selected from wound dressings, dressings for scar reduction, drug delivery devices, medical tubing, clinical surfaces, pacemaker leads, pressure sensitive adhesives, wound healing patches, wound management device, medical adhesives, catheters, shunts, valves, stents, transdermal iontophoresis patches, scaffold for tissue engineering, anti-microbial devices, ophthalmic devices, bioinserts, surgical devices, plugs, medical devices, devices for medical storage, childcare products, assisted breathing apparatus, ophthalmic devices, prostheses, reconstructive devices and body implants, wherein said product comprises a rubber or gel adhesive derived from the composition of claim 1.

29. The personal care product of claim 26 wherein said personal care component includes one or more deodorants, antiperspirants, antiperspirant/deodorants, sticks and roll-on products, skin lotions, moisturizers, toners, cleansing products, styling gels, hair dyes, hair color products, hair straighteners, nail polish, nail polish remover, sunscreen, anti-aging products, lipsticks, foundations, face powders, eye liners, eye shadows, blushes, makeup, mascaras, moisturizing preparations, foundations, body and hand preparations, skin care preparations, face and neck preparations, fragrance preparations, soft focus applications, night and day skin care preparations, tanning preparations, hand liquids, non-woven applications for personal care, baby lotions facial cleansing products, hair cuticle coats, personal care rinse-off products, gels, foam baths, scrubbing cleansers, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, drug delivery systems for topical application of medicinal compositions that are to be applied to the skin and combinations thereof.

* * * * *